United States Patent [19]

Berger

[11] Patent Number: 5,046,499

[45] Date of Patent: Sep. 10, 1991

[54] METHOD FOR MYOCARDIAL INFARCT RISK ASSESSMENT

[75] Inventor: Harvey J. Berger, Devon, Pa.

[73] Assignee: Centocor, Inc., Malvern, Pa.

[21] Appl. No.: 206,437

[22] Filed: Jun. 13, 1988

[51] Int. Cl.$^5$ .............................................. A61B 6/00
[52] U.S. Cl. .................................. 128/654; 128/659; 128/695
[58] Field of Search ................ 128/654, 659, 695, 898

[56] References Cited

U.S. PATENT DOCUMENTS 4,036,945  7/1977  Haber .................................. 128/654
4,492,753  1/1985  Shell et al. ......................... 128/637

FOREIGN PATENT DOCUMENTS 0131834  1/1985  European Pat. Off. .
0163041  12/1985  European Pat. Off. .
0268707  6/1988  European Pat. Off. .

OTHER PUBLICATIONS

DePasquale et al., "Quantitative Rotational Thallium-201 Tomography", *Circulation* 77, No. 2; pp. 316-327 (Feb. 1988).

Burow et al., "'Circumferential Profiles'", J. Nucl. Med.; vol. 20. No. 7 (U.S.A.) (Jul. 1979).

Yano et al., "Myocardial Uptake Studies ... ", J. Nucl. Med.; vol. 11 No. 11 (U.S.A.) (Nov. 1970).

"Radiochemicals Used To Scan the Heart", Chem. and Engng. News (Dec. 8, 1975).

Lerrick et al., *Circulation* 72, p. III-302; abstract 1206 (1985).

Primary Examiner—Lee S. Cohen
Assistant Examiner—John D. Zele
Attorney, Agent, or Firm—Hamilton, Brook, Smith & Reynolds

[57] ABSTRACT

The invention pertains to a method quantitative localization of antimyosin uptake in the myocardium of a patient as an indication of myocardial infarction from a plurality of planar projections displayed simultaneously. The invention also pertains to a method for screening patients with chest pain due to myocardial ischemia to identify patients having a high risk of developing myocardial infarction.

3 Claims, 4 Drawing Sheets

METHOD FOR MYOCARDIAL INFARCT RISK ASSESSMENT

FIELD OF THE INVENTION

The present invention relates to the field of cardiovascular nuclear medicine imaging and more specifically to a myocardial infarct imaging technique which is useful for identifying patients having a high risk of developing a future myocardial infarction or death.

BACKGROUND OF THE INVENTION

It has been over 25 years since mercury-203 labeled chlormerodrin was first used as an infarct-avid scintigraphic agent and the era of cardiovascular nuclear imaging began. It was not until the mid-1970's however, that imaging equipment and radiopharmaceuticals were advanced enough to make myocardial imaging a clinical reality. Technetium-99m tetracycline and technetium-99m stannous pyrophosphate were the first clinically useful infarct-avid scintigraphic radiopharmaceuticals developed. Almost simultaneously, potassium-43 was developed as the prototype myocardial perfusion tracer. Thereafter, thallium-201 imaging replaced potassium-43 for myocardial imaging, and this technique has become one of the most widely utilized procedures in nuclear medicine.

Throughout the development of the field of nuclear cardiology, particular attention has been paid to imaging myocardial necrosis. In general terms, this can be accomplished either with a "cold spot" tracer, such as thallium-201, or with a "hot spot" tracer, such as technetium-99m pyrophosphate. Technetium-99m stannous pyrophosphate and related phosphate compounds are routinely used for bone scintigraphy. Technetium-99m stannous pyrophosphate has also been utilized to image myocardial infarction in man. During the past 10 years, this radiopharmaceutical has been studied extensively by many investigators. Initial enthusiasm has waned, and the use of pyrophosphate imaging has diminished substantially over the ensuing years. While highly sensitive for Q-wave myocardial infarction, its clinical utility in patients with non Q-wave infarction or those with smaller myocardial infarcts is open to question. In addition, in order to achieve a sufficiently high sensitivity, the specificity drops significantly. Even with 10 years of history, the clinical significance of diffuse, mild to moderate uptake has not been elucidated fully. In a multicenter investigation limitation of infarct size (MILIS) sponsored by the National Heart, Lung, and Blood Institute, technetium-99m pyrophosphate imaging was included in the evaluation of all patients. In this prospective study of 726 patients with pain presumably caused by irreversible myocardial ischemia and associated with electrocardiographic changes, pyrophosphate imaging had a maximal sensitivity of 91% but a specificity of only 64%.

As a "hot spot" tracer, pyrophosphate displays the area of abnormality on a scintigraphic scan as an area of increased radionuclide uptake. On the other hand, thallium-201 displays abnormalities as "cold spots" or areas of diminished perfusion. These defects can be due to either transient ischemia or infarction, which are virtually indistinguishable on the resting and exercise thallium-201 studies. While thallium-201 imaging is highly sensitive for the detection of irreversible ischemia, especially when performed within the first six hours following the onset of chest pain, this technique cannot differentiate old from new irreversible myocardial damage. In addition, the size of perfusion defects decrease over time, such that the sensitivity of this technique for detection of myocardial infarction or ischemia is time-dependent. In fact, the extent of abnormalities seen on the resting thallium-201 study decreases significantly over the first 48 hours following infarction. Because of these known limitations, neither technetium-99m stannous pyrophosphate imaging nor thallium-201 imaging is routinely utilized in the patient with chest pain necessitating admission to the coronary care unit. Although of definite clinical utility in certain patients, these techniques cannot adequately address the primary questions being posed in the management of unstable ischemic heart disease.

SUMMARY OF THE INVENTION

The present invention provides a method for quantifying a myocardial infarction in a patient from a plurality of planar projections of antimyosin uptake. The method comprises the steps of administering an antimyosin imaging agent to the patient, quantifying antimyosin uptake in a plurality of planar images, and displaying antimyosin uptake in a bullseye image.

The present invention further provides a method for screening patients with chest pain due to myocardial ischemia to identify patients having a high risk of developing myocardial infarction. The method comprises the steps of administering an antimyosin imaging agent to the patient, displaying antimyosin uptake in a bullseye image having a preselected number of segments, and correlating the antimyosin uptake with the risk of myocardial infarction. In the present method, the step of correlating comprises classifying a patient having antimyosin uptake in less than about 30% of the bullseye display segments as a low risk patient and a patient having antimyosin uptake in about 30% or more of the bullseye display segments as a high risk patient.

DETAILED DESCRIPTION OF THE INVENTION

Figure 1:
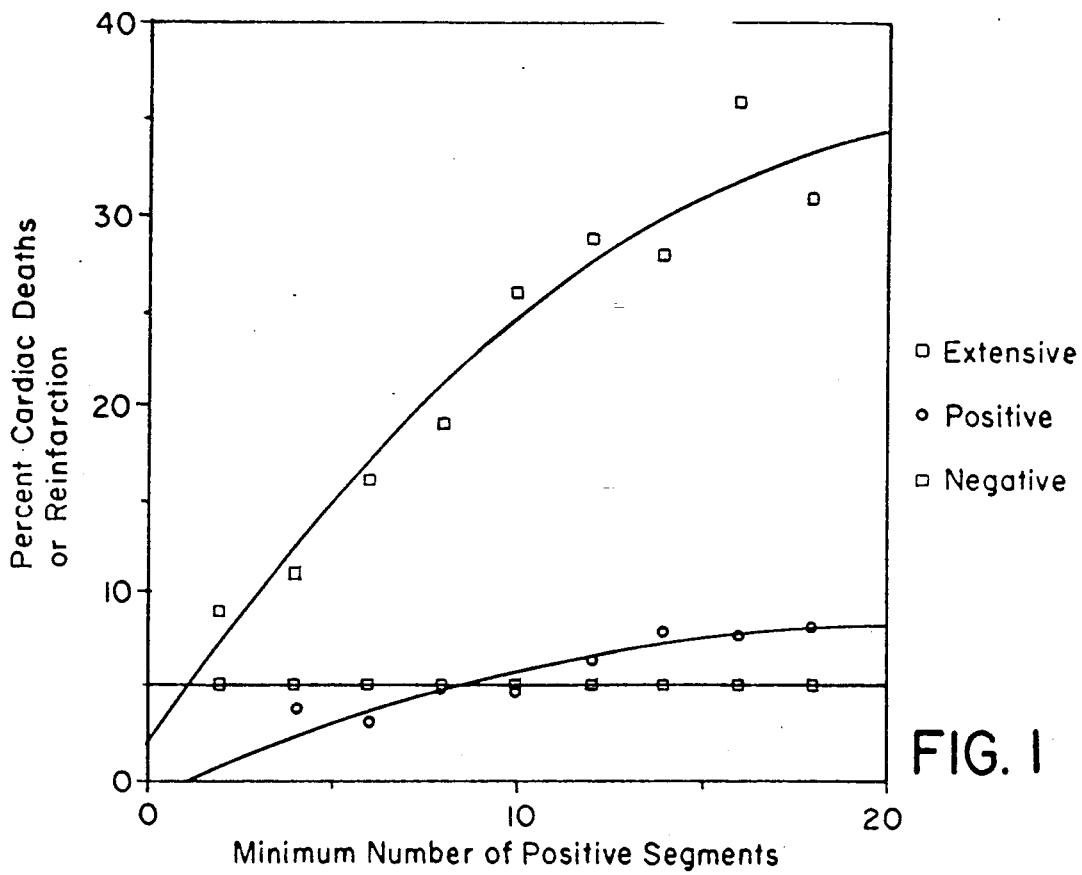
FIG. 1 shows a graph generated from the results of a clinical study described hereinafter. The graph relates the percentage of cardiac death or reinfarction to the minimum percentage of bullseye segments having antimyosin uptake.
Figure 2:
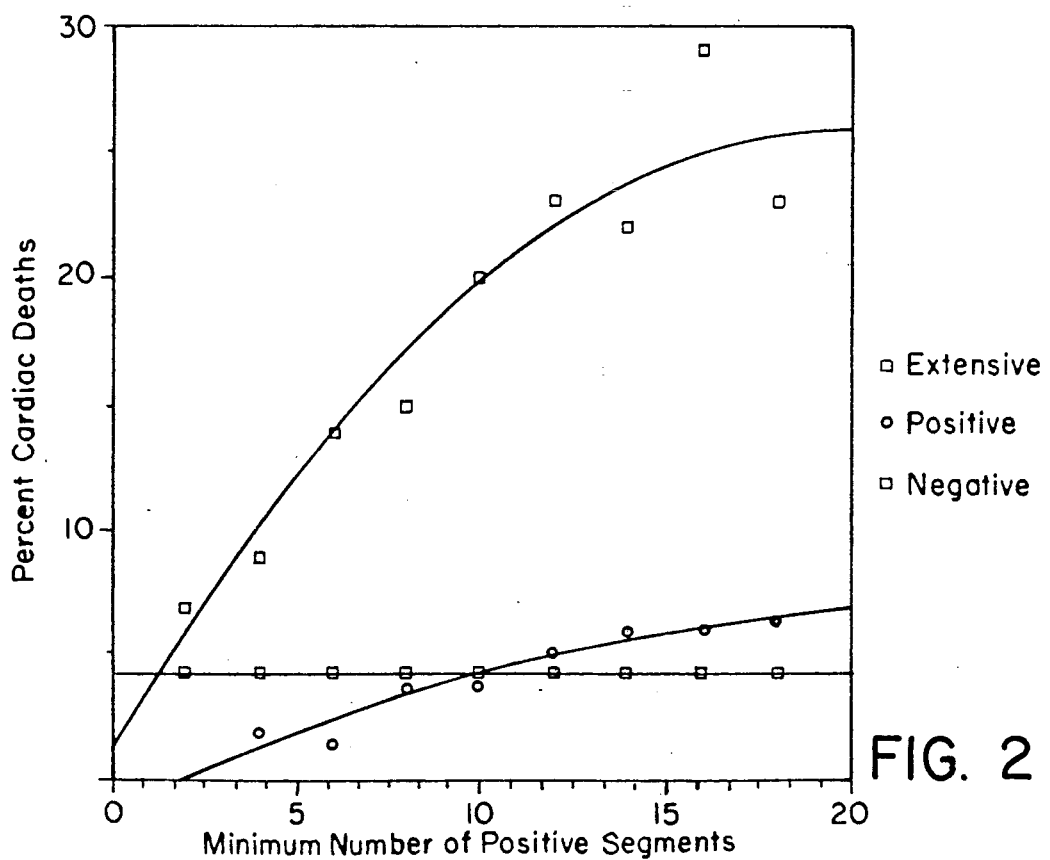
FIG. 2 shows a graph generated from the clinical study which relates the percentage of cardiac death to the minimum percentage of bullseye segments having antimyosin uptake.

The present invention provides a prognostic method for identifying patients having a risk of developing a future myocardial infarction or death. The method employs imaging and computer techniques which are readily available in virtually any clinical facility having a nuclear medicine service. It has been found that a patient having antimyosin uptake in about 50% or more of a preselected number of bullseye image segments is a patient at high risk for future infarction or subsequent death.

As used herein, the term "antimyosin imaging agent" means a pharmaceutically acceptable diagnostic composition which detects and binds to cardiac myosin in vivo and produces a localized signal detectable ex vivo. In a preferred embodiment, the diagnostic composition comprises a cardiac myosin binding protein linked to a radiolabel, and most preferably a cardiac myosin specific antibody or fragment thereof linked to a radionuclide. Such diagnostic compositions are known to those skilled in the art of nuclear medicine. In the present method, the antimyosin imaging agent is administered to a patient in an amount sufficient to provide an interpretable image of antimyosin uptake in the patient's myocardium if areas of myocardial necrosis are present. The antimyosin imaging agent is generally administered, with a pharmaceutically acceptable carrier such as normal saline, in any usual, well-known manner.

The extent of antimyosin uptake in the patient's myocardium is displayed in a bullseye image having a preselected number of segments. The expression "bullseye image" refers to a method for evaluating the in vivo distribution of a preselected diagnostic imaging agent. For example, a bullseye image which depicts the distribution of thallium-201 in myocardial perfusion imaging is disclosed in Circulation, 77:316–327, (1988), the disclosure of which is incorporated herein by reference. This method is used to display and quantify the distribution of a preselected radiotracer in a single functional image.

Visual, quantitative, and combined visual and quantitative analysis can be employed in the present method to determine the localization of antimyosin uptake in the myocardium. A plurality of planar projections of antimyosin uptake are employed to create the bulleye image of myocardial necrosis. In a preferred embodiment, three planar views of the myocardium—anterior, 40° left anterior oblique (LAO), and 70° LAO or Left Lateral—are employed to generate the bullseye image. The planar projections are displayed simultaneously on a screen or viewbox and the antimyosin uptake in each view is related to a bullseye composite map. The resulting bullseye image is divided equally into a preselected number of segments with the apex at the center and the base of the heart at the periphery. The display method of the invention maintains the normal anatomic relationship of the segments and allows one to display the three dimensional distribution of antimyosin uptake in a single functional image. This approach allows a quantitative determination of the extent of antimyosin uptake relative to the total size of the left ventricular myocardium. In a preferred embodiment, the preselected segments are displayed as a series of concentric circles with the apex at the center and the base at the periphery.

It has been found that a bullseye image having antimyosin uptake in less than about 30% of the preselected number of segments correlates to patients having a low risk of a future myocardial infarct or death, and images having antimyosin uptake in about 30% or more of the bullseye display segments correlates to patients having a high risk of a future myocardial infarct or death. The present method for screening patients having a risk of developing myocardial infarction can be employed regardless of whether the patient's clinical assessment is definitive.

The invention is further described in the following clinical study.

METHODS

Patient Population

Patients were selected for inclusion based upon the following three inclusion criteria: (1) chest pain considered to be due to myocardial ischemia; (2) age 18 years or greater; and (3) patient availability for indium-111 antimyosin administration within 48 hours of the onset of the most recent episode of chest pain.

Antibody Preparation and Administration

Antimyosin was supplied as a two vial kit. Vial I contained 0.5 mg of antimyosin-Fab-DTPA in 1 ml of 10 mM phosphate buffer, 145 mM sodium chloride, 10% maltose (w/v) (pH 6.5), with no preservatives added. Vial II contained 1.0 ml of 0.2 M citrate buffer (pH 5). Indium-111 chloride was supplied by Amersham International (Amersham, U.K.) or by Mallinckrodt Incorporated (St. Louis, Mo.) as a sterile, pyrogen-free solution with no carrier added. The antimyosin was prepared utilizing aseptic techniques.

The radiochemical purity of the indium-111 labeled antimyosin was determined using thin layer chromatography with 0.1 M sodium citrate at pH 5.0 as the buffer. The radiochemical purity was determined following radiolabelling in all instances.

Antimyosin Administration and Imaging Schedule

Patients were injected as early as possible following the onset of chest pain and meeting the entry criteria. Overall, the indium-111 dose ranged from 37.0 to 140.6 MBq (1.0 to 3 8 mCi) with a mean of $78.0 \pm 9.25$ MBq ($2.1 \pm 0.25$ mCi) in the 582 patient-studies. These values were not significantly different from those in the 497 patients included in the efficacy analysis. Although the protocol stipulated that patients not be injected later than 48 hours after chest pain, 5 patients were injected between 48 and 72 hours. The time from chest pain to injection ranged from 2.6 to 71.5 hours, with a mean $\pm$ standard deviation of $28.9 \pm 11.9$ hours. Indium-111 antimyosin images were performed at approximately 24 hours (mean, $23.6 \pm 2.8$ hours) and again approximately 24 hours later (mean, $23.2 \pm 3.1$ hours).

The earliest time of imaging ranged from 16.8 to 32.6 hours after antimyosin injection. Both sets of images were obtained as specified in the protocol in 464/497 patients. Only 24 hour images were obtained in 21 patients, while only 48 hour images were obtained in 12 patients. Planar imaging was performed using a modern gamma scintillation camera having at least 37 photomultiplier tubes, equipped with a medium energy collimator optimized for indium-111 and a sodium iodide crystal thickness of a least one-quarter inch (6 mm). Images were performed in the anterior, 45. left anterior oblique (LAO), and left lateral or 70 LAO positions. Each image was acquired for approximately 10 minutes, positioning the heart fully within the field of view and minimizing the amount of liver uptake in the image. Whenever possible, both 173 and 247 KeV photopeaks were utilized with symmetric 15–20% windows. All data were obtained in digital format.

Generation of Bullseye Image

The three standard planar views of heart—anterior, 40° left anterior oblique (LAO), and 70° LAO or left lateral—were first displayed simultaneously on a screen or viewbox. Each view of the left ventricle was then displayed graphically as an oval divided into six segments representing anatomic regions of the left ventricle. The uptake location of antimyosin on each of the images was translated onto a corresponding graphic model of the ventricle for each view.

Since the heart is three dimensional object, and the planar antimyosin images represent the heart in two dimensions, a phenomenon know as "shine through" could be seen in certain bullseye images due to superimposition of different myocardial regions. As a result, it was necessary to determine whether uptake seen in a given planar view is anatomically correct in its location or if it is caused by "shine through" from a superimposed wall of the heart. It has been found that this determination is best accomplished by confirming regional uptake by demonstrating uptake in two or more planar views. Areas of confirmed location were then transcribed to the bullseye display while areas determined to be "shine through" were not transcribed.

Figure 3A:
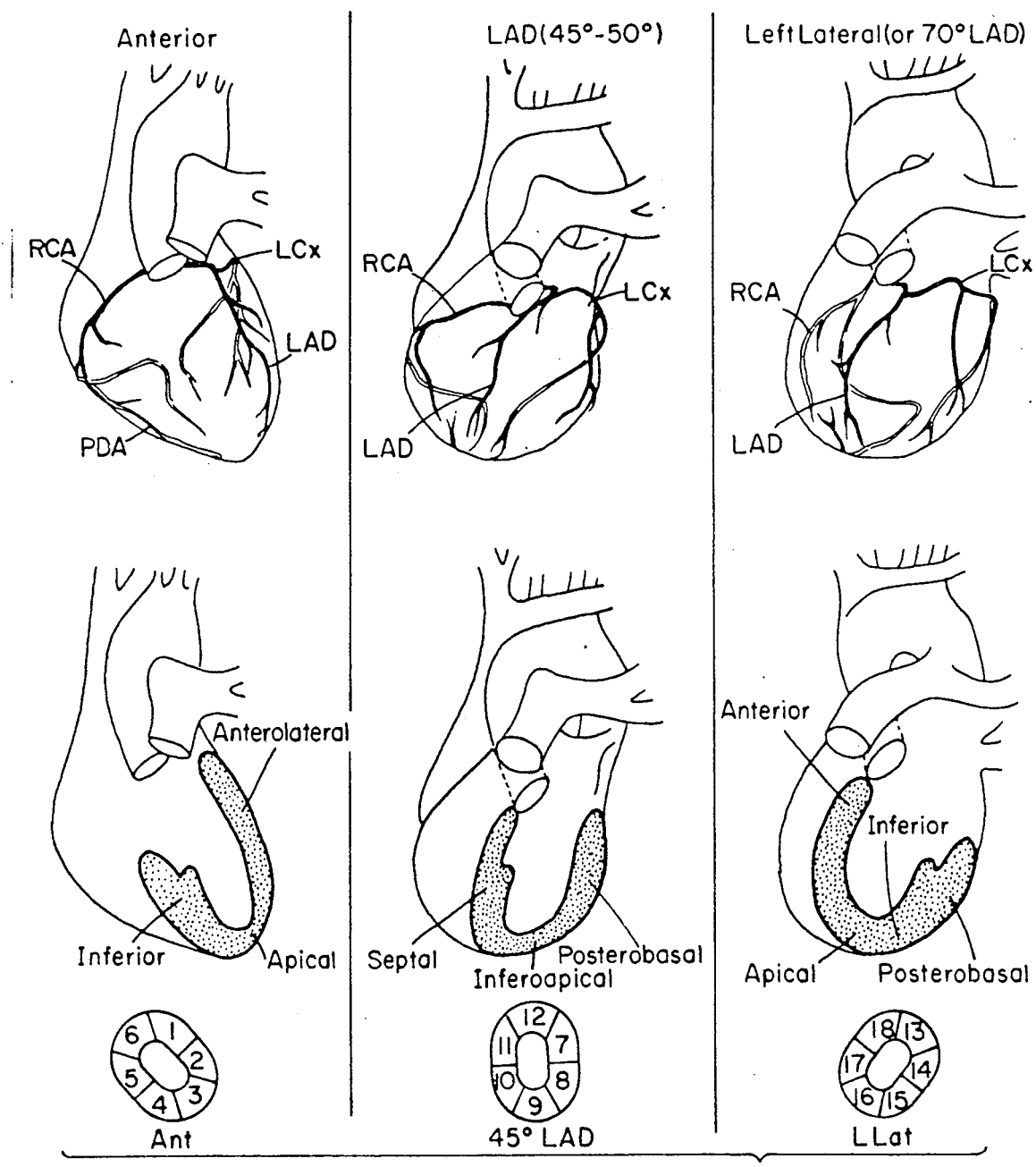
FIG. 3a shows a schematic representation of three planar views of the heart and FIG. 3b shows corresponding segments of the bulleye image employed in the clinical study.
Figure 3B:
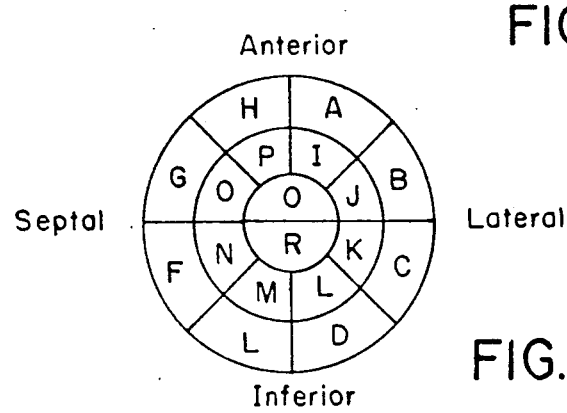
Figure 4:
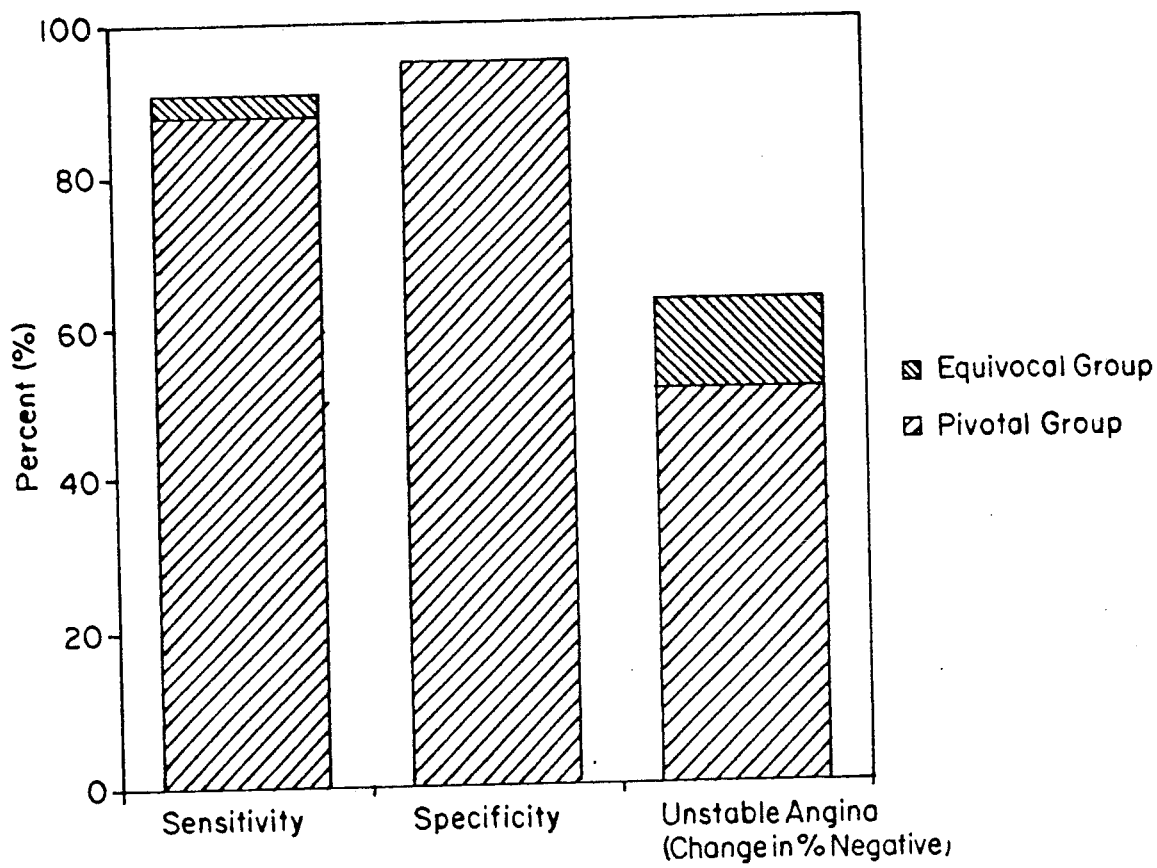
FIG. 4 shows a bar graph generated from the clinical study which represents the sensitivity and specificity of antimyosin imaging.

The shape of the left ventricle of the heart was approximated as a prolate ellipsoid divided along its short axis. The bullseye image was developed by looking at the half-ellipsoid from the pointed end with the point representing the center of the bullseye and hence the apex of the heart and the base of the half-ellipsoid representing the outer rim of the bullseye and hence the base of the heart. The segments of the planar images were numbered as shown in FIG. 3a and segmental uptake were related to the lettered segments of the bullseye image shown in FIG. 3b according to the following general scheme.

| Antimyosin Uptake in Planar Segments | relate to | Anatomic Location of the Bullseye Map |
|---|---|---|
| 1, 18 | | H, A |
| 2, 17 | | P, I |
| 3, 9, 16 | | Q, R |
| 5, 11 | | G, F |
| 4, 10 | | O, N |
| 4, 8, 10, 15 | | E, D |
| 4, 9, 16 | | M, L |
| 7, 13 | | B, C |
| 8, 15 | | J, K |

Patient Follow-up

In order to assess the relationship between the findings on the antimyosin image and major cardiac events following admission to the coronary care unit, follow-up analysis was performed. Patients were followed for up to 280 days (range 2 to 280 days, median 122 days) following injection of antimyosin. Follow-up data were obtained from review of the patient's hospital record, personal communication by the investigator with the patient's primary physician, and telephone interviews. Endpoints that were evaluated in the follow-up analysis included (a) cardiac death; (b) nonfatal myocardial infarction; (c) new onset angina pectoris and/or unstable angina; (d) medically refractory coronary artery disease requiring coronary artery bypass surgery and/or percutaneous transluminal coronary angioplasty. Follow-up was attempted for all patients entered into the study, independent of primary diagnostic categorization.

In the primary assessment of risk stratification with antimyosin, only cardiac death and nonfatal myocardial infarction were considered as "hard" endpoints. In the analysis of outcome in unstable angina, all endpoints were included. Only one "hard" event was considered in each patient, and any event occurring after the initial one was not considered. Patients who died of noncardiac causes were considered event-free until the day of their death and were included in further analyses as patients without events (censored). In the primary analysis, patients who underwent revascularization procedures post-infarction also were considered event-free until the day of their procedure and were included in further analyses as patients without events.

Methods of Statistical Analysis

All statistical tests and confidence intervals have been based upon two-sided alternative hypotheses, since no prior assumptions were made on the performance of antimyosin. Any comparison was declared to be statistically significant if the statistical test indicated that the probability of a random occurence was 0.05 or less. If the probability was between 0.05 and 0.10, this was reported but not declared to be statistically significant in discussions of the results.

Diagnostic Accuracy

Sensitivity, specificity, diagnostic accuracy, and predictive values were estimated using standard definitions, and 95% confidence intervals were constructed on these estimates, where appropriate.

Patients were assigned to one of four diagnostic categories (transmural myocardial infarction, non-transmural myocardial infarction, unstable angina, or chest pain) by an independent cardiologist who was blinded to the investigator's diagnosis and to the antimyosin imaging results. This was done to insure consistency of diagnosis throughout the study and to eliminate variability in diagnoses when pooling the results of the investigational sites. The cardiologist also determined if the diagnosis was definitive or non-definitive based on the information available in the patient's case report form. If the diagnosis was non-definitive, a reason and a secondary diagnosis were also determined. If questions arose regarding patient assignment to a diagnostic category, additional information, if available from the investigational site, was given to the cardiologist.

The final image interpretation (positive or negative), the extent, and the location of antimyosin uptake were determined by an Independent Interpretation Panel composed of five nuclear cardiologists using all available images and blinded to the information on the diagnosis of the patient. All images from a single patient were read by the same panel members.

The antimyosin scan results were reported on a bullseye image divided into 18 segments. Uptake in any segment was graded as 1, 2, or 3 from lowest to highest intensity of uptake. A scan was defined as positive if there was uptake in at least one segment on the bullseye display. A negative scan was defined as one with no uptake. One subgroup of patients was determined to have equivocal uptake and was analyzed initially as negatives and then also as positives. Another subgroup of patients was determined to have suboptimal images and was not included in efficacy analysis.

Images were obtained at approximately 24 and 48 hours following injection of antimyosin. Each of these images was determined to be diagnostic or not by the Image Interpretation Panel. If a patient had only one diagnostic image (i.e., another image was available but non-diagnostic or technically inadequate or no other image was done), this was determined to be that patient's best (most diagnostic) image. If both images were diagnostic, the image with the most definitive uptake was determined to be the most diagnostic image. If the images were equally diagnostic, the earliest (or 24 hour) image was used. A data base was created of all efficacy patients and their most diagnostic image for use in diagnostic accuracy analyses.

Sensitivity was estimated from the definitively classified patients by myocardial infarction category: transmural or nontransmural. Specificity was estimated only from the group of patients with the classification of chest pain without resting ischemia or necrosis. The antimyosin imaging results for unstable angina patients are reported as positive or negative and are discussed as a separate diagnostic group. Sensitivity was defined as the number of definitive myocardial infarction patients (broken down by type of infarct) with a positive antimyosin scan divided by the total number of definitive myocardial infarction patients. Specificity was defined as the number of patients with the definitive diagnosis of chest pain without ischemia or necrosis with a negative scan divided by the total number of definitive chest pain patients.

Prognosis Analysis

Cardiac events occurring within five months following antimyosin injection were reported using a separate follow-up form for each patient. Both the determination of the extent of antimyosin needed to classify a patient in a high risk category and the ability of antimyosin to predict a patient's death or other major cardiac-related events were examined using survival analysis techniques and categorical analyses of survival. These analyses included all efficacy patients, no patients with imaging data were excluded.

The extent of antimyosin uptake (reflected by the number of positive segments) was used in a Chi-squared analysis of all patients with either a cardiac event (cardiac death or reinfarction) within 60 days after injection or a minimum of 60 days follow-up with no cardiac event. The probability that outcome (i.e., cardiac event) is independent of uptake of antimyosin was calculated using the number of positive segments from 2 to 18. From this analysis, a risk stratification scheme was developed based on the extent of antimyosin uptake. A minimal and an optimal level of increased risk were determined based on the Chi-squared analysis.

Figure 5:
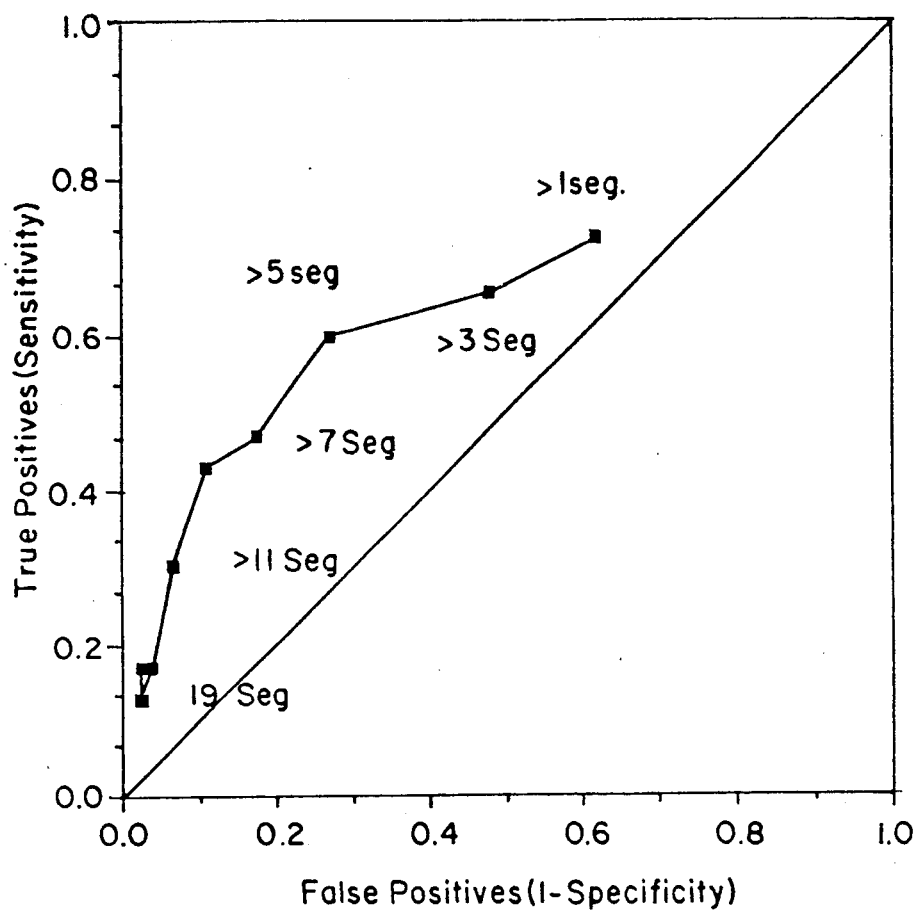
FIG. 5 shows an ROC analysis of the diagnostic performance of antimyosin relating the incidence of true positive studies to false positive studies by segment.
Figure 6:
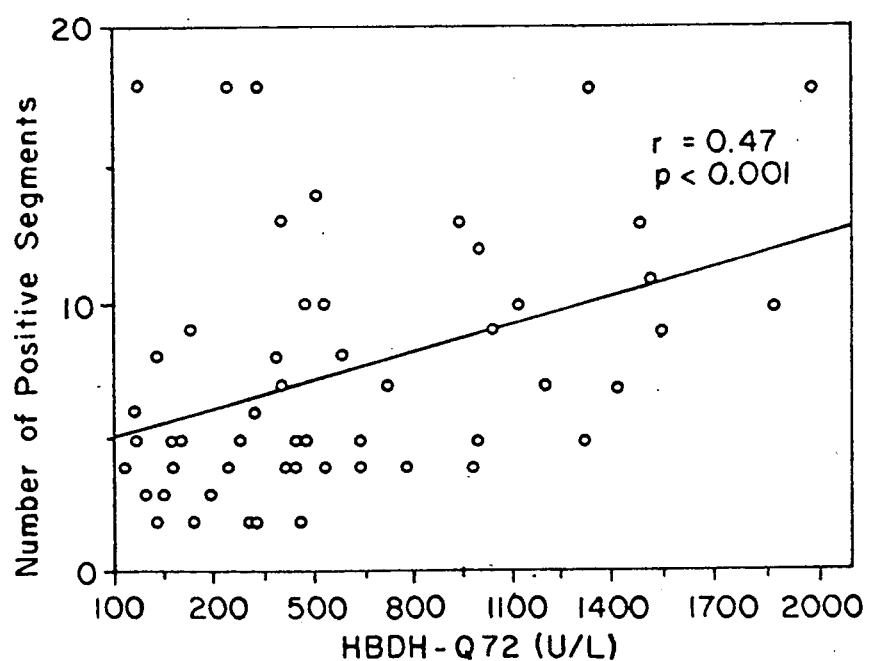
FIG. 6 shows the relationship of antimyosin uptake to enzymatic estimates of infarct size.

A receiver operating characteristic (ROC) curve was generated to examine the effect of number of positive segments on the sensitivity and specificity of antimyosin in predicting events and the results are shown in FIG. 5. This curve shows the trade-off between sensitivity (true positive rate) for diagnosing myocardial infarction at any given number of segments versus (1 - specificity) (false positive rate) for that same level. An ideal test would give a high rate of true-positive results at a level that also gives a low rate of false-positive results. The ROC curve of an ideal test would approach the upper left corner of the graph. The actual sensitivities and specificities also were tabulated.

Cox regression models were fit using a proportional hazards model to test the effects of several variables on the number of segments with uptake from the time of antimyosin injection to the time of cardiac events. Only death and nonfatal myocardial infarction were used for the pivotal analyses. The effect of the other events were examined only in the subset of patients with unstable angina using Fisher's Exact Test. Non-parametric estimates of the survival distribution and the Wilcoxon univariate and incremental chi-squared tests were used to examine the assocation of the response variable with death or nonfatal myocardial infarction. The P values for predictors and the magnitude of the chi squared correspond to the importance of the variable in predicting an increased risk for a cardiac event after accounting for all other significant predictors. Combinations of predictors were compared to using segments alone. This stepwise technique was used to establish the effect of antimyosin uptake for prognosis independent of all other clinical variables. The relative risk was calculated using different numbers of positve segments for prediction of prognosis. This relative risk can be expressed in the proportional hazards model as the exponent of the coefficient of the segments variable in the hazard equation.

Risk Stratification Based Upon the Extent of Antimyosin Uptake

The extent of antimyosin uptake represents a scintigraphic estimate of myocardial infarct size. To assess the prognostic significance of the extent of antimyosin uptake, the relationship of antimyosin uptake to post-infarct events was assessed. During the follow-up period, there were 23 cardiac deaths recorded, all occurring within 57 days after injection. This results in an overall cardiac mortality of 4.6% (23/497) for all patients admitted into the study and imaged. Excluding those patients admitted with the diagnosis of chest pain, this results in a cardiac mortality of 5.5% (23/421) in the patients with unstable ischemic heart disease. Eight of the deaths occurred within the first 10 days after antimyosin injection, seven within the next 10 days, and eight thereafter (up to 57 days later).

Life table survival analyses were carried out to test the effects of several continuous and discrete variables on the time from antimyosin injection to cardiac death or to nonfatal myocardial infarction. In these analyses, all 497 evaluable patients were included. The variables tested were: (1) the number of positive segments on the bullseye display of the antimyosin image; (2) peak creatine kinase value; (3) history of prior myocardial infarction; (4) initial Killip class; and (5) the presence or absence of Q-waves on the electrocardiogr.m. All variables were tested individually and in co:.oination. A stepwise regression procedure selected two variables as independent and additive predictors of a cardiac event: the number of positive segments on the antimyosin image and the Killip class. Prior myocardial infarction, the presence of Q-waves on the electrocardiogram, and peak creatine kinase were not significant univariate predictors of a cardiac event. The extent of antimyosin uptake had superior prognostic value as compared with Killip class or the other variables. When the number of antimyosin segments demonstrating uptake was removed from the model, there was little change in the contribution of the other variables. No combination of variables made up for the loss of prognostic power of extent of antimyosin uptake. In this survival analysis, the extent of antimyosin uptake, expressed as positive segments, adjusted for the four other factors in the model, was still highly significant ($x^2 = 11.74$, p=0.0007). These results are summarized in the following table:

| Analysis of Time to Cardiac Death or to Reinfarct in Follow Up in All Patients Evaluable for Efficacy | | | | |
|---|---|---|---|---|
| Factors Included in Model | Wilcoxon Univariate Chi-Squared | P value | Wilcoxon Incremental Chi-Squared | P value |
| Antimyosin Uptake (Number of Positive Segments) | 21.2 | 0.0001 | 21.2 | 0.0001 |
| Killip Class | 8.9 | 0.0028 | 4.6 | 0.03 |
| Prior MI | 1.1 | 0.3 | 0.5 | 0.5 |
| Q-Wave | 5.7 | 0.02 | 0.6 | 0.4 |
| Peak CK | 4.4 | 0.04 | 0.02 | 0.9 |
|  |  |  | 26.98 |  |
|  |  |  | Chi-Square |  |
| Full Model (5 factors) |  |  | 26.98 |  |
| Reduced Model (4 factors, Omit Segments) |  |  | 15.24 |  |
| Antimyosin Uptake Adjusted for 4 Other Factors |  |  | 11.74 (p = 0.0007) |  |

It has recently been suggested that the location of myocardial infarction, as opposed to extent (Q-wave or not) or infarct size, is an important predictor of prognosis following myocardial infarction. Thus, the analysis was repeated utilizing location of myocardial infarction (anterior or inferoposterior) in lieu of the presence or absence of Q-waves. This analysis included 288 patients in whom the location of myocardial infarction could be assessed (all patients with Q-wave myocardial infarction and additional patients with non Q-wave myocardial infarction in whom the location could be inferred from ST segment changes). There were 25 events in this group of patients. Once again, the number of positive antimyosin segments was highly significant, even adjusted for the four other factors ($x^2 = 18.67$, p = 0.0001). These data are summarized as follows:

| Analysis to Cardiac Death or to Reinfarct in Follow Up in Patients with Location of Myocardial Infarction Specified | | | | |
|---|---|---|---|---|
| Factors Included in Model | Wilcoxon Univariate Chi-Squared | P value | Wilcoxon Incremental Chi-Squared | P value |
| Antimyosin Uptake (Number of Positive Segments) | 14.7 | 0.0001 | 14.7 | 0.0001 |
| Location of MI | 0.05 | 0.8 | 4.7 | 0.03 |
| Killip Class | 6.6 | 0.01 | 5.1 | 0.02 |
| Peak CK | 0.7 | 0.4 | 0.5 | 0.5 |
| Prior MI | 0.4 | 0.5 | 0.06 | 0.8 |
|  |  |  | 25.15 |  |
|  |  |  | Chi-Square |  |
| Full Model (5 factors) |  |  | 25.16 |  |
| Reduced Model (4 factors, Omit Segments) |  |  | 7.49 |  |
| Antimyosin Uptake Adjusted for 4 Other Factors |  |  | 18.67 (p = 0.0007) |  |

There were nine patients with negative antimyosin images who had cardiac events (six deaths and three nonfatal myocardial infarcts during the entire follow-up period). Four of these patients had myocardial infarction (three inferoposterior Q-wave and one non Q-wave) and five had unstable angina at the time of antimyosin imaging. None of the patients underwent acute interventional procedures. Seven of the patients were Killip class I, and two were Killip class II. The peak CK in the patients with myocardial infarction ranged from 443 to 2,581 IU/ml. The remaining peak CK values were normal. One patient with myocardial infarction and one with unstable angina had equivocally positive antimyosin scans with uptake demonstrated in the inferoapical region.

What is claimed is:

1. A method for screening patients with chest pain due to myocardial ischemia to identify patients having a high risk of developing myocardial infarction comprising the steps of:
   a) administering an antimyosin imaging agent to the patient;
   b) measuring the quantity and location of antimyosin imaging agent uptake in the myocardium of the patient in a plurality of planar projections;
   c) displaying the planar projections simultaneously to generate a bullseye image having a preselected number of segments showing quantitatively the localization of antimyosin uptake in the myocardium of the patient; and
   d) correlating the antimyosin uptake with the risk of myocardial infarction wherein said step of correlating comprises classifying a patient having antimyosin uptake in less than about 30% of the bullseye image segments as a low-risk patient and a patient having antimyosin uptake in about 30% or more of the bullseye image segments as a high risk patient.

2. A method according to claim 1, wherein the antimyosin imaging agent comprises a cardiac myosin binding protein linked to a radiolabel.

3. A method according to claim 2, wherein the cardiac myosin binding protein comprises a cardiac myosin specific monoclonal antibody or fragment thereof linked to the radiolabel.

* * * * *